US008251287B2

(12) United States Patent
Kochevar

(10) Patent No.: US 8,251,287 B2
(45) Date of Patent: *Aug. 28, 2012

(54) SITE-SPECIFIC ACCESS MANAGEMENT

(75) Inventor: Peter Kochevar, Vancouver (CA)

(73) Assignee: Copper Range, Inc., Troy, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/245,644

(22) Filed: Sep. 26, 2011

(65) Prior Publication Data
US 2012/0080520 A1    Apr. 5, 2012

Related U.S. Application Data

(63) Continuation-in-part of application No. 12/273,728, filed on Nov. 19, 2008, now Pat. No. 8,025,222, which is a continuation of application No. 11/621,263, filed on Jan. 9, 2007, now Pat. No. 7,455,224, which is a continuation of application No. 10/875,657, filed on Jun. 24, 2004, now Pat. No. 7,159,778.

(60) Provisional application No. 60/482,244, filed on Jun. 26, 2003.

(51) Int. Cl.
*G06K 5/00* (2006.01)
(52) U.S. Cl. .................. 235/382; 235/487; 235/472.01; 235/462.01

(58) Field of Classification Search .................. 235/382, 235/462.01, 472.01, 472.02, 487, 486, 472.07; 705/26, 27, 14
See application file for complete search history.

(56) References Cited

U.S. PATENT DOCUMENTS

| 7,427,024 | B1 * | 9/2008 | Gazdzinski et al. | 235/384 |
| 2003/0132298 | A1 * | 7/2003 | Swartz et al. | 235/472.02 |
| 2006/0031148 | A1 * | 2/2006 | O'Dell et al. | 705/28 |
| 2007/0084919 | A1 * | 4/2007 | Petrovich | 235/383 |
| 2007/0118388 | A1 * | 5/2007 | Hamilton et al. | 705/1 |

* cited by examiner

*Primary Examiner* — Edwyn Labaze
(74) *Attorney, Agent, or Firm* — Patent Procurement Services

(57) ABSTRACT

A system for ensuring access management of a given site by providing integrated and comprehensive assessment of persons, livestock or objects that are given access to the site. The system includes a database of information about the site and potential accessors, a mobile wireless communication and scanning device to collect, retrieve and facilitate communication between a device user at the site as well as an administrator console. This system is flexible enough to maintain current information about the persons, livestock or objects requesting access to the site and communicating those results to the device user in real time. The system is further enabled through the Internet and the World Wide Web.

20 Claims, 2 Drawing Sheets

SITE-SPECIFIC ACCESS MANAGEMENT

CROSS-REFERENCE TO RELATED APPLICATIONS

This application is a continuation-in-part of U.S. patent application Ser. No. 12/273,728 filed Nov. 19, 2009, now U.S. Pat. No. 8,025,222, which in turn is a continuation of U.S. patent application Ser. No. 11/621,263 filed Jan. 9, 2007, now U.S. Pat. No. 7,455,224, which in turn is a continuation of U.S. patent application Ser. No. 10/875,657 filed Jun. 24, 2004, now U.S. Pat. No. 7,159,778, which in turn claims priority of U.S. Provisional Patent Application 60/482,244 filed Jun. 26, 2003, which are incorporated herein by reference.

FIELD OF THE INVENTION

The present invention relates to the field of access management for enabling, tracking and controlling authenticated access of people or things to a protected area. Specifically, this invention relates to a method of providing access management for a given site consistent with a predetermined set of rules as well as the system for implementing such method.

BACKGROUND OF THE INVENTION

It is well known in the art that security is a primary consideration prerequisite for the peaceful enjoyment of the fruits of freedom and the survival of individuals and organized bodies alike. For example, to promote security, it is imperative to keep doors and windows locked at home, to keep automobiles locked and secured by alarms, and, generally, to be aware of one's surroundings while walking on streets, driving in automobiles or the like, and shopping in malls or in stores. Also, to promote security for commercial establishments, and public places such as libraries, courthouses and government buildings, it is imperative to provide full-time guards, limited access via X-ray machines or biometrics screening devices, etc.

Devices and methods for the promotion of safety and security of persons and property are well known in the art. The most common of these devices may be those used to protect homes and automobiles. The more basic of these monitor the opening of doors and sound an alarm if the device has not been disabled. While there has been little advance in home security devices, automotive security devices have undergone significant improvements from the conventional automobile alarm in recent years to match the rise in the value of these vehicles.

A recent development related to automobile security is the incorporation of vehicle tracking systems like the LOJACK® which utilizes a transmitter installed in the vehicle to emit radio waves to a receiver tuned to a given frequency receivable by the police for tracking. An improvement on this takes advantage of the Global Positioning System (GPS) to provide location information of the automobile and furthermore enables the appropriate security personnel to provide personal security in the form of a panic button in case of an emergency. Yet another improvement on vehicle tracking systems is the On-Guard tracking system or its equivalent. This device utilizes GPS and cellular technology to provide vehicle location, speed and direction to a central monitoring station. On-Guard also offers several non-emergency related services including navigational and roadside assistance services.

Further advances in automotive related security systems are such that are disclosed by U.S. Pat. No. 5,430,432 teaching of a device that monitors a vehicle for unsafe driver conditions and provides real-time warning, and if uncorrected, makes a record of the occurrence.

Devices used to monitor people, as opposed to vehicles, are also well known. Perhaps the most familiar application of such a device pertains to the concept of house arrest. Typical house arrest devices operate by detecting when the subject, who is wearing a transmitter, moves too far from a receiver located in his or her home or other place of detainment. If the receiver does not receive the transmitted signal or receives a signal significantly attenuated due to the distance between the receiver and the transmitter, an auto-dialer is triggered to alert the proper authorities. Such a device used to track people offers many practical and useful applications beyond the monitoring of criminals. Children, Alzheimer patients, the mentally retarded, the disabled, infirm individuals, and other similarly situated persons may be monitored and located should they become lost.

Personal security devices are also well known. The most common personal security device is the small container with a panic button, implemented via pull cord, grenade-type ring, or other means easily actuated but difficult to reset. When the panic button is actuated, a loud sound is emitted to scare off attackers and or alert nearby people to a potential emergency. Another personal security device, well known for its advertising with an elderly person who has fallen and can't get up, uses a necklace worn panic button and auto-dialer. These devices operate by requiring the user to actuate the panic button in the event of an emergency, thereby initiating the auto-dialer which contacts the appropriate authorities and delivers a prerecorded message.

Medical monitoring devices are also well known. They are used in clinics, hospitals, and doctors' offices around the world. They often are able to give early warning to medical professionals of impending adverse health conditions, where the individual does not even sense the decline until significantly later, after the situation has significantly progressed, the individual suddenly feeling terrible, debilitated, or worse. Many times, the relaxed and controlled hospital environment can reduce or eliminate the sources of adverse health conditions, such as exertion, stress, noise, toxins, diet, etc. Accordingly, more sophisticated medical monitoring devices have been developed which are miniaturized, battery-operated versions of hospital equipment for home or ambulatory use, such as electroencephalogram (EEG) machines, electrocardiogram (EKG) machines, blood pressure, sugar, or oxygen saturation monitors, and the like. While these portable machines monitor vital body functions in a real world situation, they merely record this information. The most sophisticated known variants of these devices can take the recorded information, digitize it, and then modulate the information back onto an analog carrier signal, which can then be transmitted to a central station via simple acoustic coupler modem.

Prior art teaches of security systems to enable access of an individual to a protected area like a car. The Aslanidis et al., U.S. Pat. No. 6,690,259, teaches a security system to enable authenticated access of an individual to a protected area, using a remote control unit with a transponder, carried by the individual which transmits identification code group on reception of an interrogation signal. Access to a protected area is granted only on positive verification of the right to access.

Prior art also teaches a system for security and auditing of persons or property. U.S. Pat. No. 5,825,283 discloses a device that tracks the location of a subject, be it person or object, and compares the actual location with predefined or stored geographical boundaries representing locations that are less than safe or secure, and alerts the device user or other designated personnel that the tracked subject has gone outside its geographical boundaries.

U.S. Pat. No. 6,690,259 discloses a security system to enable authenticated access of an individual to a protected area, including a remote control unit with a transponder, carried by the individual, which transmits an identification code group on reception of an interrogation signal. Access to a protected area will only be permitted on positive verification of the right to access.

In U.S. Pat. No. 5,745,036, prior art also teaches an electronic article security system and anti-theft device for stores that uses intelligent tags, surveillance cameras and transaction data to protect products within a security area or detection zone.

U.S. Pat. No. 6,735,695 discloses a biometrics security method and apparatus that restricts the ability of a user to access a device or facility using a portion of biometric data to validate the user's identity.

Needless to say, the safety and security of people and things continues to be of paramount importance in society, especially in light of new dangers posed by terrorist threats. As the foregoing clearly shows, the safety and security industry has responded with increasingly innovative ideas for dealing with new and old challenges. Prior art has taken advantage of various technological advances in the GPS field, cellular technology, computer technology, radio-wave technology and a host of others to improve our ability to provide more effective security devices, methods and processes. Collectively, prior art includes strong solutions for securing people and things, tracking locations, as well as recording and transmitting information of a given subject or location. But there are limitations.

Today, the typical security access process validates the rights of a person or thing at the door, gate or point of entry. This validation occurs in many ways including visual acknowledgement of a subject's access rights against, say, an access card. This access card/badge may or may not have the photograph of the individual on it. Oftentimes, validation is simply against pre-encoded information that is electronically read from the user's access card/badge or security tag. In either case, the user's rights are predetermined and are based on very basic information collected and stored at some earlier point in time. More sophisticated security access processes incorporate biometric data or other unique characteristics of the subject into the validation process. Although they can be very robust, these types of processes offer limited security because the information, like a drug test result or safety clearance, about the bearer of the access card/badge or security tag may become stale rather quickly. Additionally, the card/badge or tag and related data may become compromised, resulting in access to the wrong person or thing. Besides, the existing solutions do not adequately deal with the situation where the subject has compromised or found a way to bypass the security at the entry point. In addition to the typical lack of currency in the validation data, the data and related process are typically isolated within the defined location. The existing solutions offer incomplete data exchange and fixed security entry points incapable of responding to the ever-changing real life situation and stimulus. Therefore, redundancy and limited integration abound within the safety and security establishment, and there is great difficulty in assessing and understanding the level of security risk a person or thing poses to the collective.

What is needed in the art is a more robust safety and security system that is integrated and flexible, that not only allows for authentication of people or things at a point of entry, but is also mobile and capable of providing real-time information about the subject to safety and security officials. Accordingly, these limitations and disadvantages of the prior art are overcome with the present invention.

SUMMARY OF THE INVENTION

This invention teaches an improved system and method for site-specific safety and security. The present invention provides an integrated security platform for protecting different sites by enabling access to people, livestock or things based on a customized set of rules. It also provides security officials the opportunity for real-time, continuous, mobile or random authentication or revalidation of access rights of people or things.

In one embodiment of the present invention a site-specific safety and security system is provided. A "site" is deemed herein as any closed geographical area where entry of people or things is governed by a set of rules. Some examples of a site are a governmental authority controlled area, such as a country, a military base, or a building; a workplace; an airport departure area; and any entertainment venue.

DETAILED DESCRIPTION OF THE INVENTION

Figure 1:
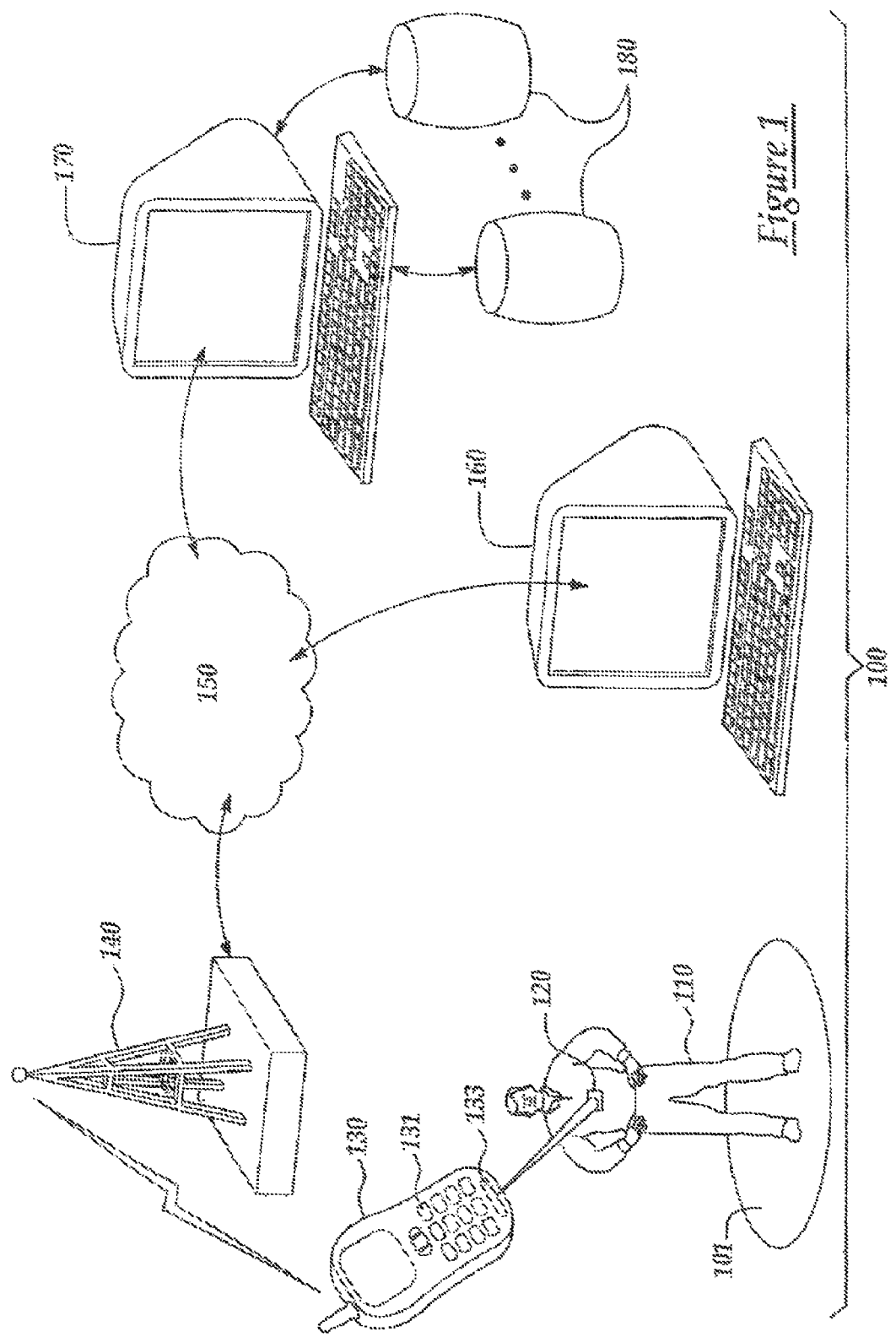
FIG. 1 is a schematic site-specific access management system.

The present invention has utility as a system and process for providing site-specific safety, security, or inventory consistent with a given set of rules. The invention takes advantage of technological advances in various fields of endeavor to enable robust site management in an integrated manner.

An inventive system provides verification that people, livestock or objects present at a site are compliant with whatever rules the site administrator establishes for legitimate presence at the site including permission to be in the area. For instance, if a person, livestock, or object requires a certification to be present within the area, a scan of an identifier datum associated with the person, livestock, or object is checked against a remote database by wireless communication via a network. Based on the time of a scan event, a remote database is optionally updated to serve as a tracking system or work reporting time clock across disparate areas and large organizations, or similarly to track inventory movement into, out of, or within an area. As a system administrator receives scan events in essentially real time, a scanner user can be provided with real-time instructions as to how to deal with an individual person, livestock, or object within moments of the initial scanning event. The result is more efficient management of people, livestock, and objects.

An inventive system is well suited for environments such as job site control and tracking livestock through the food handling chain. The inventive system includes a scanning device coupled to a wireless communicator in communication with a base station by way of a network such as the Internet, an intranet, or a local area network. The scanning device reads at least one tag or optionally provides manually keyed information that is compared against and/or updates a remote database coupled to the base station. An application server is optionally placed intermediate between a remote database and a network, the server functioning as an interface therebetween and as a platform on which to run with greater efficiency operational software.

Advantageously, the present invention would attempt to authenticate a request for access into a closed geographical area on behalf of a person or thing. In establishing the security environment in an area, a number of resources have to be in place. These include an integrated application system environment to support the peripheral communication and data manipulation devices. Additionally, a site operator is provided with an appropriate mobile wireless communication and scanning device that is identified to the database. A person, livestock, or object identifier datum is uploaded by the wireless communication and scanning device for ultimate comparison against a database. It is appreciated that an identifier datum according to the present invention is a personal identification number (PIN) such as a social security number keyed by a person directly into an inventive mobile wireless communication and scanning device; a manifest or invoice number keyed or scanned into an inventive mobile wireless communication and scanning device; and a physical characteristic of the person, livestock or object such as an output from a device such as an iris scanner, a fingerprint scanner, a digital camera, a temperature gauge, a gas chromatograph, a mass spectrometer. Preferably, a person, livestock or object to be scanned is previously defined to the database and carries an identifier datum in a form directly readable by the scanning device, the form of the datum illustratively including a barcode, radiofrequency tag, or the like. Alternatively, the scanning device is manually keyed to communicate with the database and/or base station. Additionally, the "site" is defined to the database by some geographical characteristics, coordinates like longitude and latitude obtained from a GPS-type reading, or a geographic location associated with a scan event by a particular scanning device.

Once these resources have been allocated, the system is ready to support site-specific safety and security requirements. For example, a person obtains a badge from a system administrator and goes to a site. Site security personnel attempt to authenticate the person to the site using a wireless communication device to scan pre-encoded information on the badge. The device signal requests the application to query the database. Preferably, the application is run on an application server. More preferably, the remote database resides on a database server. In an exemplary mode, the request from the scanning device first authenticates the device, saves the scan information in the administration database for future use, authenticates the site using transmitted GPS coordinates, then extracts the applicable site rules. These site rules are used to determine what information is to be extracted from the compliance database. Based on the person/object-specific information delivered by the device, the application determines the person/object's compliance status with the specific site rules. The result of the compliance check is sent back to the wireless communication and sampling device, including name and compliance status which is rendered on the device's display with an appropriate audible tone consistent with the status indicator.

The advantages of the present invention include elimination of redundancy in data kept of individuals accessing registered sites, provision of interactive validation or authentication capability to a site's safety and security personnel, robust databases with more robust and current administrative and compliance data on site and subject, an integrated environment for all registered sites and subjects, and the ability to revalidate an access right to a given site even after initial authorization. Because of the robust databases and extensive data collected, the present invention offers additional significant advantages due to reporting capability. Operational robustness of the present invention, which lowers the probability of a critical failure in the system, is realized through the introduction of redundant (more than one) parallel communication networks and redundant backend systems including application servers and databases. Furthermore, additional scanners may be provided in case of a scanner failure, as well as multiple entry and exit points to and from a work site or secured venue. Application servers and databases can all be replicated so that if an application server or database fails, replicants can be brought online immediately to take over the task of the failed backend component. Furthermore, customer or user experiences are improved during system interaction by reducing latency, which is the cycle time between scanning a person or thing seeking entry to a site, and the actuation of some apparatus at the site to either allow or deny entry, and the broadening the types of scanning interactions that may take place at site entry or exit portals.

While the present invention is detailed hereafter with respect to site access management, it is appreciated that the present invention is readily adapted to address other applications illustratively including tracking foodstuffs through the chain of production and retail, package delivery systems, drug dispensation in a medical facility setting, just-in-time manufacturing inventory management, and pre-cleared customs service operation.

The present invention teaches of a system for securing sites against access by unwanted people and/or things. Such a system is depicted in FIG. 1 generally at 100. A wireless communications and scanning device 130 is used at a site 101 to gather input about a person, livestock or an object 110, and compare the input to reference information present in one or more databases $180_{1\ to\ N+1}$, where N is the number of redundant or backup databases. The implementation of backup databases ensures the availability of access and verification data, even if the primary database fails, or is out of communication contact with the scanning device. The databases $180_{1\ to\ N+1}$ may be located in the same facility, or for added security may be placed in separate locations. The data stored on the replicated databases $180_{1\ to\ N+1}$ are kept in sync to ensure that whatever database is in contact with the scanning device 130 provide the most accurate and up to date information available. The databases $180_{1\ to\ N+1}$ are appreciated to include application-specific information that illustratively includes compliance information, administration information, inventory information, or combinations thereof. Based on the results, safety and security officials may allow a person or thing under consideration into the site, or they may bar a person or thing from the site either permanently or until some discrepancy with the site's rules has been corrected.

The combined wireless communications and scanning device 130 within the present invention 100 is a custom fabricated unit or alternatively is built using commercial off-the-shelf components. One example of a wireless communications and scanning device that uses off-the-shelf components is a programmable, Internet-ready, cellular telephone or is coupled to an access control structure such as a turnstile. An identifier datum about a person, livestock or object 110 at a site 101 is input via the phone keypad 131, or it might be input via some attached sensor, such as a barcode scanner 133. Other types of sensors operative herein illustratively include biometric measuring devices such as an iris scanner, a fingerprint scanner, a digital camera, a temperature gauge, a gas chromatograph, a mass spectrometer and the like. An alternative device 130 is also operative with infrared (IR), radio frequency (RF), BLUETOOTH®, or WiFi communication transponders.

In the case of a digital camera or measuring tools, a scanning device 130 samples information identifier data directly from the person, livestock, or object 110. In the case of a barcode scanner, IR, RF, BLUETOOTH®, and WiFi transponders, the person, livestock or object 110 at a site 101 has attached a "tag" or badge 120 that was issued by an administrator. The badge 120 is inert in that it is printed or embossed with certain associated identifier information such as a name, employee serial number, a barcoded representation of an employee or part number, a photo, or the like. This information is optionally sampled directly by a scanning device 130 or it may be read by a person and then manually input using an input device including a keypad, stylus, touchpad, or the like. A badge 120 optionally also encapsulates associated identifying information electronically that is read by a scanner 130, or the badge 120 optionally actively broadcasts this information itself to a receiver located in the scanning device 130.

The examples given above for a wireless communications and scanning device 130 within an inventive system 100 are mobile devices that might be carried by site compliance and security officials. For instance, a foreman at a construction site might scan a barcoded badge 120 of members of his work crew at the start of each work day using his cellular telephone having an attached barcode reader. Alternatively, the wireless communications and sampling device has a stationary component that interacts with a mobile component residing with the people, livestock, or object 110 being screened for site compliance. For instance, a person at a site 101 might be issued badge 120 that is a transmitter device such as a cellular telephone, IR, RF, BLUETOOTH® or WiFi transmitter. An "active" badge 120 also contains personal information stored electronically that is sent to receivers positioned at specific points around the site 101, such as the entrances. These stationary receivers would then be connected to the Internet or other network either in a wired or wireless fashion. Feedback about compliance would then be sent back to monitoring stations associated with the stationary receivers that would be viewed by site compliance and security officials.

Associated or inherent identifier data that is collected by an inventive access management system wireless communications and scanning device 130 is transmitted to application servers $170_{1\ to\ N+1}$, where N is the number of redundant or backup application servers, along with an indication of where and when the identifier data was collected. The implementation of backup databases ensures the availability of access and verification data, even if the primary application server fails, or is out of communication contact with the scanning device 130. The application servers $170_{1\ to\ N+1}$ may be located in the same facility, or for added security may be placed in separate locations. The application servers $170_{1\ to\ N+1}$ compare the identifying information with a set of reference data for the same person, livestock, or object that was collected by an inventive system administrator at some prior point in time. As will be explained further below, the first of the N+1 application servers to be in contact with the scanning device 130 handles the information request. If there is a match, then the compliance information for the person or thing in question is retrieved from appropriate databases by the application server. In addition, the collected information transmitted to the application server by the wireless communications and scanning device 130 is stored in the N+1 databases for future use in preparing site or compliance reports for an inventive system. It is appreciated that an application server and database copy are optionally integrated in an inventive communications and sampling device. In this integrated embodiment, the sampling device queries its own onboard database scanning the data presented for access and verification, there is no need for device authentication from a remote database $180_{1\ to\ N+1}$. However, an integrated device that is in communication with a network or multiple networks that keeps the local, integrated device database up-to-date and in sync with other database copies; during this synchronization process, device authentication is required.

The location information that is optionally provided by the wireless communications and scanning device 130 may be input by an operator manually using a keypad to punch in a location code, a selector to choose an item from a menu, a reader to scan location barcodes from some type of atlas, or the like. The location information is preferably provided automatically by the communications and scanning device 130 through some form of measurement. For instance, the communications and scanning device 130 incorporates a GPS unit, or the device 130 is able to determine position using some combination of triangulation, direction determination, and range finding while in communication with some collection of beacons whose positions have been predetermined, or each device 130 is assigned to a predetermined site 101.

Once one of the application servers $170_{1\ to\ N+1}$ has made a determination regarding a person, livestock or object 110 in question, the server packages the result into a form that can be easily rendered by whatever client device 130 initiated the query and transmits results back thereto. The result information might include an indication of whether or not a person, livestock or object was known to the system 100, and if known, associated identifying information such as custom details including name, photo, serial number, or the like is optionally transmitted back to the device 130. In addition, the result information includes some indication of whether a person, livestock or object 110 is or is not compliant with the presence rules established for a site, and if not compliant, the reason therefor.

The kind of information and its form that is transmitted back to a wireless communications and scanning device 130, or any other network client device in communication with the application servers $170_{1\ to\ N+1}$, is different depending on who is using the devices. For instance, a construction foreman with a cellular telephone/barcode scanner combination might only see the name, photo, and a yes/no indication of compliance for a person that he just scanned. On the other hand, a system administrator sitting at a desktop computer 160 optionally sees the complete work histories, the results of all tests, and all personal information for any individual registered within the system 100. Yet again, a safety engineer working for an organization might be able to see the same information as the administrator but only for employees who work for the same organization, or contractors thereto, as the engineer.

The databases $180_{1\ to\ N+1}$ within the system 100 contain information about the people, livestock, or objects that may be present at a site 101. It is appreciated that the number of networks, application servers, and databases need not be equivalent and optionally varying numbers of networks, servers, and databases are interactive and operative in the present invention. Reference numerals provided in the accompanying drawings are intended to denote a varying number of such networks, servers, and databases; which such duplicates of each omitted for visual clarity. Some of the information is collected by a system administrator during some registration process prior to allowing people, livestock or objects 110 into a site 101 so as to serve as reference information for use during compliance checking. The rest of the information is collected at a site each time a person, livestock or object 110 seeks entry to the site 101. Database information might be information that is associated with people, livestock or objects including names, descriptive words or phrases, identification numbers, addresses, phone numbers, e-mail addresses, company affiliations, contact information for guardians or overseers, or combinations thereof. Database information might also consist of data representing measurements of inherent qualities of people, livestock or objects illustratively including weights, dimensions, electromagnetic reflectance or emission properties, photographs, chemical or material composition, or temperature; and specific to people, measured data illustratively includes fingerprint encodings, iris scans, and facial photos. Finally, the databases $180_{1\ to\ N+1}$ would also contain site rule compliance information such as the results of any tests performed by or on people or things. The databases $180_{1\ to\ N-1}$ of the inventive system 100 are optionally synced with other of the databases $180_{1\ to\ N+1}$ or separate databases (not shown) by way of conventional software protocols, such as those for example detailed in U.S. Pat. No. 7,747,784. For people, this compliance information might include results of drug, safety, and job certification tests as well as other more general personal information such as police records, presence on sexual offender lists, credit histories, etc. For objects, compliance information might include the results of product certification tests, the presence on banned substance lists, histories of usage, etc.

The wireless communications and scanning device 130 is connected to one or more networks $150_{1\ to\ N+1}$, where N is the number of redundant or backup networks, by way of one or more base stations $140_{1\ to\ N+1}$, where N is the number of redundant or backup base stations. For example, multiple base stations or cellular modems may be in communication contact with scanner 130, and scanner 130 may simultaneously send data over all available N+1 networks in an effort to reach the one or more application servers $170_{1\ to\ N+1}$. A scanner might send the same sampled data simultaneously over all the networks it is connected to, each data stream tagged with the same unique transaction ID. The backend upon receiving multiple data samples would act on the first it receives and disregard any subsequent samples having the same transaction ID already in the database. Transaction ID's can consist of some unique scanner ID and a timestamp. Alternatively, a scanner 130, with access to redundant networks, can instantly and seamlessly failover to one of the other N−1 networks to remain in communication with the backend system. Using one or more of the networks, the wireless and communications and sampling device connects to one or more application servers $170_{1\ to\ N+1}$, which act as the coordinators for all tasks performed within the system 100. Programs running on the application servers $170_{1\ to\ N+1}$ receive input from the wireless communications and scanning device 130 and then place measured or sampled information into the databases $180_{1\ to\ N+1}$ and pose queries to the database $180_{1\ to\ N+1}$ on behalf of the device. The programs running on the application servers $170_{1\ to\ N+1}$ also package query results into data formats that can be rendered easily on the wireless communications and scanning device 130. It is appreciated that each communications and sampling device optionally has more than one modem or transceiver built-in for use with different networks. Each such modem or transceiver would communicate with its own base station and each modem may have its own IP address and thus a unique identifier for a sampling device of an inventive system is optionally the concatenation of the sorted IP addresses of the device associated modems.

When a sampling device makes a scan, the scan data is optionally sent by each modem in the sampling device, using a modem specific network, to one or more communicative application servers. It is appreciated that an application server optionally gets hit multiple times for the same data verification scan transaction. In certain inventive configurations, an application server acts on the first request it receives for a given transaction identification and ignores the rests. A similar circumstance optionally occurs on the sampling device when multiple application servers respond back after a scan. The application servers in this system structure preferably include the transaction identification in their responses, and the sampling device acts on the first message it receives for a given transaction identification and ignores any others. This is particular preferred, in instances when the sampling device is a turnstile and the message it receives dictates whether to open a gate because of verified access data.

A system administrator configures the system 100 and sees reports about specific people, livestock, or objects 110 and sites 101 using administrator consoles 160 that connect to the application server 170 over the network using some network facility like the World Wide Web. A network client, such as a Web browser running on a desktop computer, is one example of an administrator console 160 when the Web browser is pointed at an administrator Web site. An administrator console 160 communicates with the application server 170 much in the same manner as does the wireless communications and scanning device 130. In other words, database updates and query results are performed by programs running on the application server 170 on behalf of administrators using the network clients on a console 160.

The responsiveness or reduction in latency of the system 100, as exhibited through quicker responses to scanner information requests may be accomplished by distributing databases, and moving some of the data copies closer to where scanning takes place. In an extreme case, a database copy can be placed on a scanner itself so that no network communication need take place to check scanned data against reference data in the database, thereby virtually eliminating any potential latency. As with the mention of redundant databases above, with the distribution of data among database copies, the copies must be kept current and consistent (in synch) between stored databases. For example, if scanners are being used at a sports venue and a person purchases an e-ticket at the last minute from a ticket agent, the access rights for that person must be securely communicated by the ticket agent in short order to all scanners at the venue. Thus all databases must be updated to reflect the purchase of the e-ticket.

Figure 2:
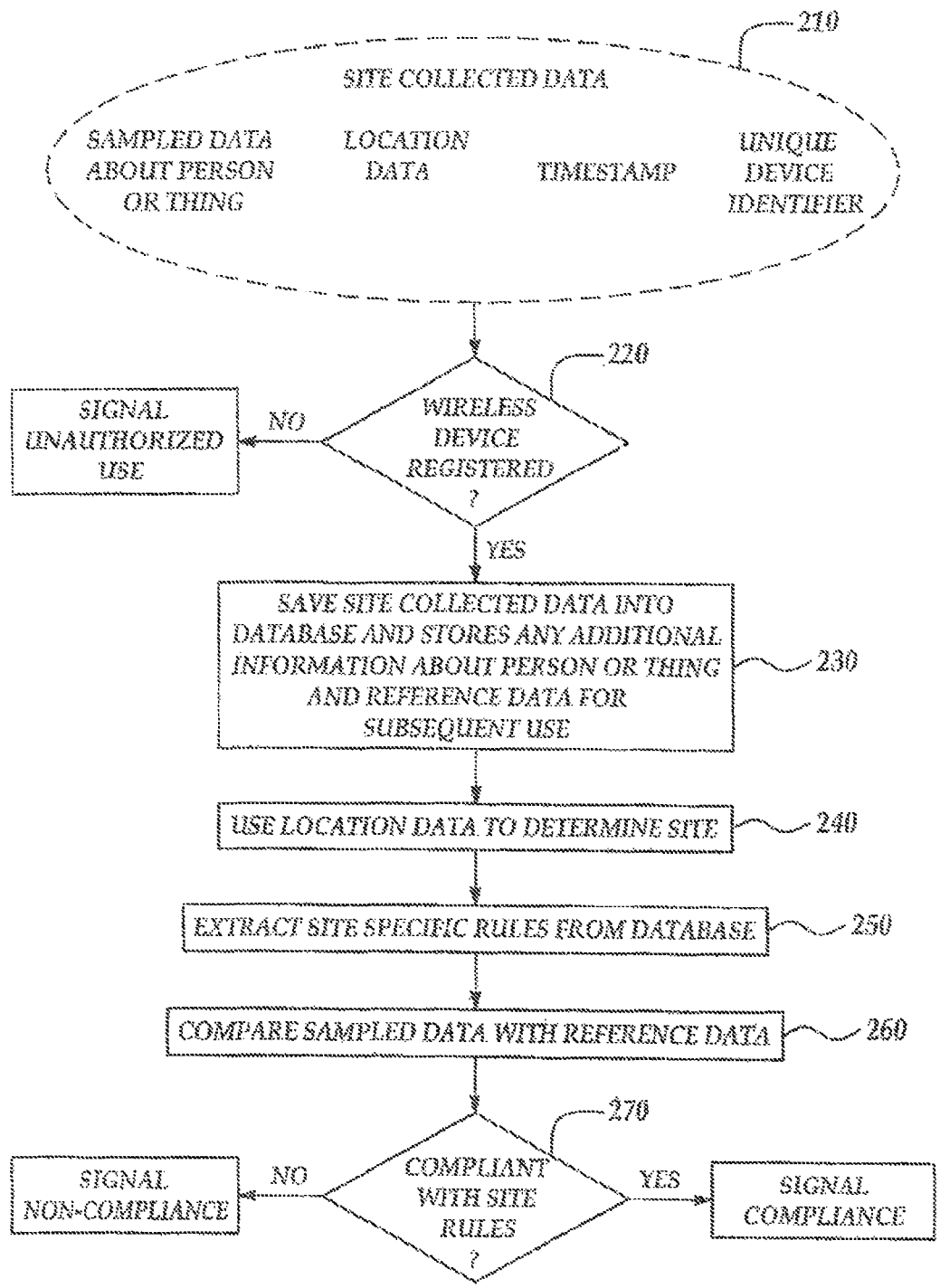
FIG. 2 is the site compliance flowchart, depicting the process for authenticating a person or thing to a given site and simultaneously refreshing the collected information about the person or thing.

FIG. 2 depicts a typical site compliance process for authenticating a person, livestock or object's access to a given site. It assumes that certain data has been previously collected about the site including sampled data about person or thing, location data timestamp and unique device identifier 210.

The authentication process starts with the wireless device sending a signal and request to the base station. An application program determines whether or not the signal is from a registered device 220. If it is not a registered device, a signal is returned to signify unauthorized use. Otherwise, the device is recognized to the site and certain data including location data is collected about the site and stored into appropriate databases. Additional information about the person or thing is also stored as reference data for subsequent use 230.

Based on the location data just collected, information about the site from which the request was made is determined 240. Using site-specific information thus retrieved, site-specific rules are extracted from appropriate databases 250. The application program compares the sampled data 210 with the reference data 230 to determine if the subject is compliant with site rules 260, and the signal is thus returned to the device indicating compliance or non-compliance of the subject with site rules 270.

One example of an inventive system uses a programmable, Internet-ready cellular telephone that also contains a GPS chipset as the basis for the wireless communications and sampling device. One such phone that meets these criteria today is the Motorola i88s handset. Attached to the handset would be a barcode scanner, such as Symbol Technologies' PSM20i barcode scanner that is made specifically for the i88s handset. A program running on the handset would handle all communication between the handset user and the rest of the system. This program would make use of vendor supplied application programmers interfaces (API) that interact with the handset GPS chipset and the attached barcode scanner.

This inventive system realization is then used to check compliance with a set of work rules established for a given workplace. Each person that enters a workplace would carry an identification badge issued previously by a system administrator. This badge would have imprinted on it a barcode encoding of the badge owner's system identification number, and the person's name and affiliation. Workplace compliance and safety officials would scan the barcode on the identification badge using their phone/scanner device.

Alternatively, persons entering the workplace may own their own or be issued cellular telephones, or other portable devices capable of near field communication (NFC). For example, a construction worker seeking entry to a job site would no longer need to carry a plastic ID card, rather the worker could hold up their NFC-enabled cell phone at an entry point instead. In another example, a car might be outfitted with a transceiver capable of transmitting some identifier, such as its vehicle identification number (VIN), which a scanner at a parking lot can receive in order to check if the car has the right to enter.

After a successful scan, indicated by an audible beep on the handset, the program running on the handset would then contact the application server using the Internet and the HTTP communications protocol. The information passed by the handset to the application server consists of the identification number scanned from the badge, the current latitude and longitude of the handset gathered from the handset GPS chip set, the time and date at which the scan took place, and some unique alphanumeric identifier for the handset.

The system application server is a standard World Wide Web server augmented with an engine for running computer programs to service requests, for example, the Tomcat application server developed by the Apache Software Foundation. Upon receiving scan information from a handset, the application server starts an application program to service the request. This program first checks an administration database for a registered handset having the same unique identifier as the handset that made the request. This unique identifier could be the fixed IP address of the handset, its IMEI number, the handset telephone number or some number generated by the system, or some combination of these numbers. All handsets used with the inventive application are assumed to be registered with the system in that their unique identifier has been previously recorded in the system administration database by a system administrator.

Once a handset has been authenticated, the application program saves the scan information in the administration database for possible use in summary reports for system administrators. Next, the application program determines at what workplace the scan took place by comparing the latitude and longitude of the handset with the latitudes and longitudes of the registered workplaces in the administration database.

Once a workplace has been identified by the application program, the program then looks up what work rules apply for that workplace in the administration database. These rules determine the information that must be sought in the compliance databases for the person that was scanned. For instance, a particular workplace may require that all personnel on site must have passed a drug test within some period of time from the current date, and all personnel might have had to pass a battery of safety tests as well. The test results are gathered out of the compliance databases using the identification number of the person that was scanned, and any time-related information from the databases is compared with the timestamp of the scan. The compliance information was stored previously by an administrator who administers the various tests that may be required of personnel who might visit a registered area workplace.

The results of the compliance check by the application program are sent back to the handset as a reply to the HTTP request. The results consist of an indication of whether or not a person with the scanned identification number exists in the compliance database, and if they do, the person's name and an indication of whether or not they are compliant with the workplace's work rules is included as well. These results are then rendered on the handset's display screen and an audible tone is sounded that is different depending on the type of result.

To help verify that a person who was scanned is who they say they are, the workplace compliance and security official with the handset may optionally request a photo of the person to be displayed on the handset. These photos are digital images of personnel that would have been taken previously by a system administrator and stored in the administration database when the personnel were registered with the system.

Following a successful scan, a person gaining entry or exiting a venue or work site may be issued a receipt. The receipt could be hardcopy or electronic. The receipt might list details of the entry or exit transaction, and it may include additional information that a person, entity, or thing can use after gaining entry to and exiting from a site. For instance, in the case of a person entering a sports venue, the receipt might contain their section and seat number, and coupons to make or suggest purchases of items available for sale at the venue, or for future discounts to future games or events. In addition, a receipt on entry to a sports or entertainment venue might also contain a coupon that can be redeemed by the venue-goer for a reduced price meal at a nearby restaurant. Electronic receipts might be emailed to a person, texted to them on their cell phone, be held in some online account that a person may have (e.g., social networking sites such as Facebook), etc. The printed receipt may have a quick response (QR) barcode that a user can capture with their wireless device to be taken to a web site with information on a product or service.

A system administrator may at any time view summary reports of the information contained in the administration and compliance databases. These reports are put together by applications running on the application server, and administrators gain access to these reports by contacting the server using a Web browser. Administrators must first authenticate themselves to the server by entering a username and password on the administrator's home page. Once authenticated, an administrator may request any one of a number of reports of a set type. The list of report types is different depending on what role an administrator has. For instance, super users have access to all report types while compliance officers working for specific companies only have access to report types that pertain to personnel who work at the same companies as the compliance officers. Examples of such reports include the list of names and personal information of all personnel working at a given workplace on a given date, and the list of names of personnel working at any workplace on a given date who are not compliant with the workplace's work rules.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A site-specific access management system comprising: a mobile wireless communications device;
   at least one identifier datum, wherein said datum is transmitted by said wireless communications device;
   a plurality of redundant base stations receiving wireless communication of said datum from said wireless communications device, wherein said plurality of base stations are connected to a plurality of networks;
   a plurality of redundant application servers connected to said networks, and
   a plurality of redundant databases accessed by an application program, said application program running on said plurality of application servers to compare said datum with information in said plurality of databases,
   said mobile wireless communications device authenticated by sending a request to said plurality of base stations running said application program authenticating said mobile wireless communications and scanning device as registered to access said plurality of databases.

2. The system of claim 1 wherein said datum is at least one of a barcode, a manually keyed alphanumeric value, or a biometric.

3. The system of claim 1 wherein said datum is selected from a group consisting of: weight, temperature, dimension, electromagnetic reflectance, gas concentration, and chemical composition.

4. The system of claim 1 wherein said wireless communications device sends copies of said datum simultaneously over said plurality of networks, each of said copies of said datum tagged with the same unique transaction ID; and
   wherein one of said plurality of application servers upon receiving said copies of said datum acts on a first copy from said copies of said datum received, and disregards any subsequent datum from said copies of said datum with the same transaction ID already in the plurality of databases.

5. The system of claim 1 wherein said Transaction ID comprises a unique scanner ID and a timestamp.

6. The system of claim 1 wherein said wireless device automatically switches between each of said plurality of networks in response to a failure of one or more of said plurality of networks.

7. The system of claim 1 wherein said plurality of application servers are located in a single location.

8. The system of claim 1 wherein said plurality of application servers are located in separate locations.

9. The system of claim 1 wherein data stored on said plurality of databases are kept in sync to ensure that whichever one of said plurality of databases is in contact with said wireless device provides the most accurate and up to date information available.

10. The system of claim 1 further comprising an administration console in communication with said plurality of application servers.

11. The system of claim 10 wherein said application program responds to a request from said wireless device, and said application program responds to requests from said administrator console.

12. The system of claim 10 wherein said application program has computer logic for producing a report about people, livestock or objects present at said site.

13. The system of claim 12 wherein said report is communicated via one of said plurality of application servers to at least one of: said device and said administration console.

14. The system of claim 1 wherein said site is a workplace or a livestock processing plant.

15. The system of claim 1 wherein at least one of a time of scan and global positioning system coordinates are communicated and stored in said plurality of databases.

16. The system of claim 15 further comprising a second identifier datum that differs from the at least one of a time of scan and global positioning system coordinates that provides a tracking system within said application program.

17. The system of claim 1 wherein said wireless device is in communication with a portable device configured with near field communication (NFC).

18. The system of claim 17 wherein said portable device is a transceiver capable of transmitting an identifier or a cell phone.

19. The system of claim 1 wherein said wireless device is configured to issue a receipt in response to a person, entity, object, or animal gaining entry or exiting a venue or work site.

20. The system of claim 19 wherein said receipt lists at least one of details of the entry or exit, seating information, an advertisement, or a coupon.

* * * * *